(12) United States Patent
Hirao (10) Patent No.: US 7,239,904 B2
(45) Date of Patent: Jul. 3, 2007

(54) COMPONENT CONCENTRATION MEASUREMENT METHOD AND DEVICE

(75) Inventor: Konomu Hirao, Kyoto (JP)

(73) Assignee: Arkray, Inc., Kyoto (JP)

( * ) Notice: Subject to any disclaimer, the term of this patent is extended or adjusted under 35 U.S.C. 154(b) by 168 days.

(21) Appl. No.: 10/514,785

(22) PCT Filed: May 7, 2003

(86) PCT No.: PCT/JP03/05724

§ 371 (c)(1),
(2), (4) Date: Nov. 8, 2004

(87) PCT Pub. No.: WO03/095988

PCT Pub. Date: Nov. 20, 2003

(65) Prior Publication Data

US 2005/0171415 A1    Aug. 4, 2005

(30) Foreign Application Priority Data

May 8, 2002    (JP) .............................. 2002-133265

(51) Int. Cl.
*A61B 5/00*    (2006.01)
(52) U.S. Cl. ...................................... 600/316; 600/310
(58) Field of Classification Search ................ 600/310, 600/316, 322
See application file for complete search history.

(56) References Cited

U.S. PATENT DOCUMENTS 5,871,442 A * 2/1999 Madarasz et al. ........... 600/316
6,166,807 A * 12/2000 Kawamura et al. ......... 600/316
6,466,320 B1 10/2002 Kawamura et al.
6,640,116 B2 * 10/2003 Diab .......................... 600/322

FOREIGN PATENT DOCUMENTS

| JP | 5-176917 | 7/1993 |
|---|---|---|
| JP | 9-138231 | 5/1997 |
| JP | 9-145605 | 6/1997 |
| JP | 2000-258338 | 9/2000 |
| JP | 2000-346840 | 12/2000 |
| JP | 2002-82046 | 3/2002 |

* cited by examiner

*Primary Examiner*—Eric F Winakur
(74) *Attorney, Agent, or Firm*—Hamre, Schumann, Mueller & Larson, P.C.

(57) ABSTRACT

The invention relates to measuring the concentration of a target component in an object. The invention provides a component concentration measurement method including a first step in which light is irradiated onto a measurement object held in a first magnetic field state for detecting the light from the object, a second step in which light is irradiated onto the object held in a second magnetic field state different from the first state for detecting the light from the object, and a third step in which the concentration of the target component is calculated based on the detection results in the first and the second steps. The first magnetic field state may be a magnetic-field-modulated state, while the second state may be a non-magnetic-field-modulated state.

31 Claims, 6 Drawing Sheets

COMPONENT CONCENTRATION MEASUREMENT METHOD AND DEVICE

TECHNICAL FIELD

The present invention relates to a technology for measuring a target component in an object of measurement.

BACKGROUND ART

In recent years, there has been an increase in people suffering from lifestyle-related diseases such as diabetes, and hence there has been an increase in the need to measure blood sugar level, cholesterol level and so on in one's blood based on a simple technique that can be carried out at home and so on. As a simple technique for measuring blood sugar level, there is for example a method in which a fingertip is punctured so that blood flows out and a sample is taken, and then the glucose concentration in the blood is measured using this sample.

However, puncturing one's fingertip is accompanied by pain, and hence measuring the blood sugar level may be painful. In particular, in the case of a diabetes sufferer, to carry out blood sugar level management during everyday life, the blood sugar level must be measured several times a day. A diabetes sufferer may thus be subjected to pain several times a day, and hence measuring the blood sugar level is a great burden for a diabetes sufferer. Moreover, with ordinary glucose concentration measurement, there is a problem that consumables such as biosensors or urine test paper are used.

In Japanese Patent Application Laid-open No. H05-176917, to reduce the burden during glucose concentration measurement, there has thus been disclosed a method of measuring the blood sugar level without taking blood from a patient. With this method, near-infrared light of wavelength 0.78 to 1.32 μm is irradiated onto a human body, and the glucose concentration can be measured based on the intensity of the light transmitted through the human body.

On the other hand, in Japanese Patent Application Laid-open No. H09-138231, there has been disclosed a method of measuring the glucose concentration in urine without the need for consumables such as urine test paper. With this method, light that has passed through a polarizer is irradiated onto a sample solution, and the glucose concentration can be measured based on the angle of optical rotation of the light transmitted through the sample solution at this time.

However, with the method disclosed in Japanese Patent Application Laid-open No. 5-176917, the measurement is prone to being affected by the state of optical scattering when the irradiated light is transmitted through the human body. That is, variation in measurement results between individuals arises due to differences in the state of optical scattering between individuals, and moreover even with the same person, variation in measurement results arises due to differences in the state of optical scattering at different measurement sites. To resolve these problems, a calibration line must be prepared for each individual, and moreover for each person measurement must be always be carried out at the same site.

On the other hand, with the method disclosed in Japanese Patent Application Laid-open No. H09-138231, the method is effective for measurement on a solution that does not contain solid matter, but there is a problem in that in the case of trying to carry out measurement on a turbid liquid such as blood or trying to measure a component in biological tissue, the measurement is affected by optical scattering due to solid matter in the object of measurement, and hence accurate measurements cannot be obtained.

DISCLOSURE OF THE INVENTION

It is an object of the present invention to accurately measure a target substance component concentration in an object of measurement, with the influence of scattering matter contained in the object of measurement excluded as much as possible, and while reducing the burden on the measurer.

In a first aspect of the present invention, there is provided a component concentration measurement method comprising: a first step of irradiating light onto an object of measurement with the object of measurement in a first magnetic field state, and detecting the state of light from the object of measurement at this time; a second step of irradiating light onto the object of measurement with the object of measurement in a second magnetic field state different to the first magnetic field state, and detecting the state of light from the object of measurement at this time; and a third step of calculating the concentration of a target component based on the detection result in the first step and the detection result in the second step.

Preferably, the first magnetic field state is a magnetic-field-modulated state obtained by applying a magnetic field to the object of measurement from outside, and the second magnetic field state is a non-magnetic-field-modulated state. In this case, the first magnetic field state is, for example, attained by applying a magnetic field to the object of measurement such that the magnetic flux density at the center of the luminous flux of the light irradiated onto the object of measurement is 100 to 1000 gauss. The second magnetic field state may of course also be a magnetic-field-modulated state.

The light irradiated onto the object of measurement is preferably linearly polarized light.

In the first and second steps, for example the state of light from the object of measurement is detected after making the light into linearly polarized light using an analyzer. In this case, the analyzer preferably has a polarization axis disposed so as to selectively transmit linearly polarized light having a different oscillation plane from the oscillation plane of the linearly polarized light emitted from the light irradiator. Specifically, the analyzer is preferably disposed in a state with the polarization axis thereof shifted by 1.0 to 10.0° in terms of the absolute value from a position of the polarization axis of the analyzer at which the amount of light transmitted by the analyzer is lowest when light is irradiated onto the object of measurement in the second magnetic field state.

In the first and second steps, for example the state of light from the object of measurement is detected as the absorbance or the amount of light. In this case, the absorbance or the amount of light is measured based on light transmitted through the object of measurement.

In the third step, for example the concentration of the target component is calculated based on the difference Δ between the absorbance or the amount of light measured in the first step and the absorbance or the amount of light measured in the second step.

In this case, preferably, in the third step, the coefficient $\alpha_1$ and the coefficient $\beta_1$ in the undermentioned equation are determined, and the concentration of the target component is calculated based on the coefficients $\alpha_1$ and $\beta_1$.

$$\text{Difference} \Delta = \alpha_1 \times X_1 + \beta_1 \times Y_1 \quad (1)$$

$X_1$: Change in absorbance due to change in state of optical rotation for target component between first and second magnetic field states.

$Y_1$: Change in absorbance due to state of optical rotation for at least one component other than target component between first and second magnetic field states.

Here, $X_1$ can for example be determined by subtracting the change in the absorbance for a reference from the change in the absorbance for the object of measurement, and $Y_1$ can be determined as the change in the absorbance for the reference.

In the case of measuring blood sugar value, $X_1$ in equation (1) may be determined as the change in the absorbance due to a change in the state of optical rotation for glucose between the first and second magnetic field states, and the calculation may be carried out with the term $\beta_1 \times Y_1$ in equation (1) represented by undermentioned equation (2).

$$\beta_1 \times Y_1 = \beta_{11} \times Y_{11} + \beta_{12} \times Y_{12} + \beta_{13} \times Y_{13} \quad (2)$$

In equation (2), $\beta_{11}$, $\beta_{12}$ and $\beta_{13}$ are respectively a coefficient for plasma, a coefficient for oxyhemoglobin and a coefficient for reduced hemoglobin, and $Y_{11}$, $Y_{12}$ and $Y_{13}$ are respectively the change in the absorbance due to a change in the state of optical rotation for plasma, oxyhemoglobin and reduced hemoglobin between the first and second magnetic field states.

In the first and second steps, a spectrum may be obtained by measuring the absorbance or the amount of light at a plurality of wavelengths for the object of measurement and a reference. In this case, in the third step, the difference $\Delta$ is obtained as a spectrum, and the coefficient $\alpha_2$ and the coefficient $\beta_2$ in the undermentioned equation are determined, and the concentration of the target component is calculated based on the coefficients $\alpha_2$ and $\beta_2$.

$$\text{Difference} \Delta = \alpha_2 \times X_2 + \beta_2 \times Y_2 \quad (3)$$

$X_2$: Spectrum of change in absorbance due to change in state of optical rotation for target component between first and second magnetic field states.

$Y_2$: Spectrum of change in absorbance due to state of optical rotation for at least one component other than target component between first and second magnetic field states.

Here, $X_2$ can for example be determined by subtracting the spectrum of the change in the absorbance for the reference between the first and second magnetic field states from the spectrum of the change in the absorbance for the object of measurement between the first and second magnetic field states, and $Y_2$ can be determined as the spectrum of the change in the absorbance for the reference between the first and second magnetic field states.

In the case of measuring blood sugar value, $X_2$ in equation (3) may be determined as the spectrum of the change in the absorbance due to a change in the state of optical rotation for glucose between the first and second magnetic field states, and the calculation may be carried out with the term $\beta_2 \times Y_2$ in equation (3) represented by undermentioned equation (4).

$$\beta_2 \times Y_2 = \beta_{21} \times Y_{21} + \beta_{22} \times Y_{22} + \beta_{23} \times Y_{23} \quad (4)$$

In equation (4), $\beta_{21}$, $\beta_{22}$ and $\beta_{23}$ are respectively a coefficient for plasma, a coefficient for oxyhemoglobin and a coefficient for reduced hemoglobin, and $Y_{21}$, $Y_{22}$ and $Y_{23}$ are respectively the spectrum of the change in the absorbance due to a change in the state of optical rotation for plasma, oxyhemoglobin and reduced hemoglobin between the first and second magnetic field states.

The coefficient $\alpha_2$ and the coefficient $\beta_2$ can be determined, for example, based on a singular value decomposition procedure.

An example of the reference when determining $X_1$, $X_2$, $Y_1$ and $Y_2$ is pure water. As the reference, one in which a state containing noise components (light-diffusing components other than the target component and pure water) is constructed in pseudo fashion can also be used.

There are no particular limitations on the target component of which the concentration is measured, but examples are glucose, cholesterol, lactic acid, ascorbic acid, and so on.

The target component of which the concentration is measured is typically glucose, and in this case the wavelength of the light irradiated onto the object of measurement is selected from a range of 780 to 1320 nm.

The first and second steps can be carried out by irradiating light directly onto an object of measurement present in a human body. The first and second steps can of course also be carried out in a state with the object of measurement held in a measurement cell.

In a second aspect of the present invention, there is provided a component concentration measurement device comprising light irradiator for irradiating light onto an object of measurement, magnetic field applier for applying a magnetic field to the object of measurement from outside, light receiver for receiving light from the object of measurement, and calculator for calculating the concentration of a target component contained in the object of measurement based on the result of light reception by the light receiver.

Preferably, the light irradiator is constituted such as to emit linearly polarized light. In this case, the light irradiator is for example constituted as a laser light source.

As the light irradiator, a titanium sapphire laser can be used.

The component concentration measurement device of the present invention preferably has a constitution further comprising an analyzer for making light to be received by the light receiver into linearly polarized light.

The analyzer preferably has a polarization axis thereof disposed so as to selectively transmit linearly polarized light having a different oscillation plane from the oscillation plane of the linearly polarized light emitted from the light irradiator.

The component concentration measurement device of the present invention may have a constitution further comprising a controller for controlling the intensity of the magnetic field applied from the magnetic field applier.

The magnetic field applier has a constitution comprising for example a rotating magnetic plate or an electromagnet.

The component concentration measurement device of the present invention may have a constitution further comprising fixer for fixing the light irradiator, the magnetic field applier and the light receiver with a desired positional relationship relative to a predetermined site on a human body. In this case, the fixer is constituted for example such as to be suitable for fixing onto a fingertip or an earlobe.

BEST MODE FOR CARRYING OUT THE INVENTION

The best modes for carrying out the present invention will be described below with reference to the drawings.

Figure 1:
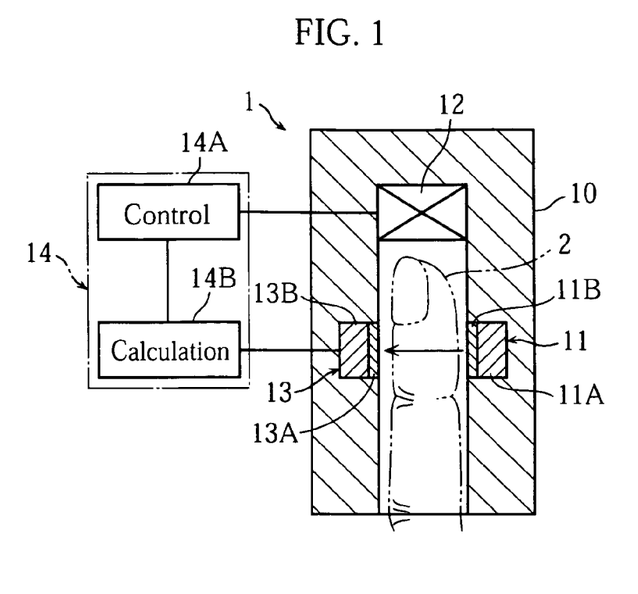
FIG. 1 is a sectional view in which some parts of a concentration measuring device according to a first embodiment of the present invention are drawn as blocks.
Figure 2:
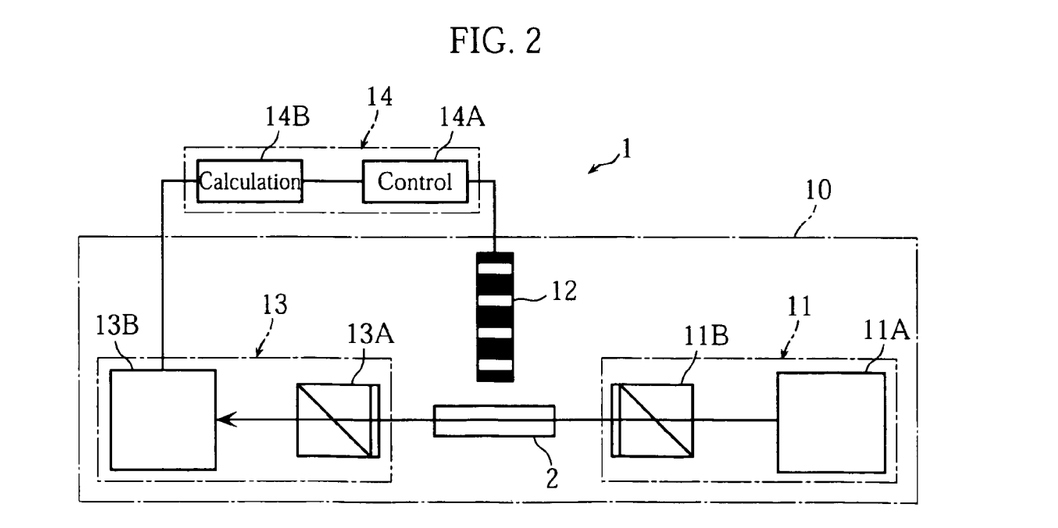
FIG. 2 is a conceptual view of the concentration measuring device shown in FIG. 1.

Reference is first made to FIGS. 1 and 2 illustrating a first embodiment according to the present invention.

A concentration measuring device 1 shown in FIG. 1 is constituted such as to non-invasively measure the concentration of a target component, for example glucose or cholesterol, in a body fluid in a fingertip 2. The concentration measuring device 1 comprises a fingertip holding section 10, a light irradiating section 11, a magnetic field applying section 12, a light receiving section 13, and regulating circuitry 14.

The fingertip holding section 10 is for holding the fingertip during analysis, and includes at least the light irradiating section 11, the magnetic field applying section 12 and the light receiving section 13.

The light irradiating section 11 is for irradiating light onto the fingertip 2. The light irradiating section 11 includes a light source 11A and a polarizer 11B.

The light source 11A, constituted so as to emit light over a broad wavelength range, comprises a halogen lamp or a titanium sapphire laser, for example. In the case of using a halogen lamp as the light source of the light irradiating section 11, the light irradiating section 11 is constituted such that the light from the halogen lamp is filtered using a color filter or the like, thus selecting light of a target wavelength before emitting the light. In the case of measuring glucose concentration, light of a wavelength selected from a range of 780 to 1320 nm is irradiated onto the object of measurement.

The polarizer 11B is for filtering through linearly polarized light having a targeted oscillation plane from out of the light emitted from the light source 11A.

The magnetic field applying section 12 is for applying a magnetic field to the body fluid present inside the fingertip 2, i.e. the object of measurement, and is constituted, for example, so as to comprise a rotating magnetic plate. The rotating magnetic plate is provided with a plurality of magnets, for example eight neodymium magnets, disposed at equal intervals around an outer peripheral portion of the plate.

The light receiving section 13 is for receiving, out of light transmitted through the fingertip 2, linearly polarized light oscillating in a specific direction, and outputting a signal in accordance with the amount of light received. The light receiving section 13 comprises an analyzer 13A, and a photoreceiver 13B.

The analyzer 13A filters the light transmitted through the fingertip 2, selectively allowing the passage of linearly polarized light having the specific oscillation plane. In the case that rotated light is to be received by the photoreceiver 13B, the analyzer 13A is disposed such that the polarization axis thereof is non-parallel to the polarization axis of the polarizer 11B.

The photoreceiver 13B is for receiving light that has passed through the fingertip 2 and the analyzer 13A, and outputting, for example, an electrical signal in accordance with the amount of light received, and is constituted, for example, as a photodiode or a phototransistor.

The regulating circuitry 14 is for controlling the operation of relevant elements, and comprises a control section 14A and a calculation section 14B.

The main function of the control section 14A is to control the magnetic field applying section 12. Specifically, the control section 14A causes the magnetic field applying section 12 to select between a state in which a magnetic field is applied to the object of measurement and another state in which a magnetic field is not applied, and further controls, when a magnetic field is applied to the object of measurement, the magnitude of the applied magnetic field. In the case, for example, that the magnetic field applying section 12 comprises a rotating magnetic plate, the control section 14A controls the angle of rotation of the rotating magnetic plate, thus controlling the magnetic field state realized in the object of measurement.

The calculation section 14B is for calculating the concentration of the target component in the object of measurement based on the amount of light received by the photoreceiver 13B. With the calculation section 14B, for example the concentration of the target component is calculated based on the amount of light received by the photoreceiver 13B in a state in which a magnetic field is not applied to the object of measurement, and the amount of light received by the photoreceiver 13B in a state in which a magnetic field is applied to the object of measurement.

Such regulating circuitry 14 is, for example, constituted from a CPU, a ROM and a RAM.

In the concentration measuring device 1, as shown in FIG. 2, light irradiated from the light source 11A is made into linearly polarized light by the polarizer 11B, and is then irradiated onto the fingertip 2. Moreover, the magnitude of a magnetic field externally applied to the fingertip 2, more precisely the body fluid (object of measurement) inside the fingertip 2, is controlled through the control of the control section 14A. Typically, the modulation frequency is made to be 10 to 100 Hz such that the magnetic flux density at the center of the luminous flux is 100 to 1500 gauss, and a first magnetic field state in which a magnetic field is applied to the object of measurement, and a second magnetic field state in which a magnetic field is not externally applied to the object of measurement are selected between.

At the photoreceiver 13B, light having a targeted oscillation plane that has passed through the fingertip 2 and the analyzer 13A is received. An electrical signal is outputted from the photoreceiver 13B in accordance with the amount of light received, and this is stored in the calculation section 14B. In the calculation section 14B, the amount of light received when the object of measurement is in the first magnetic field state, and the amount of light received when the object of measurement is in the second magnetic field state are stored separately.

As is clear from the tests described later, the extent to which optical rotation occurs in the object of measurement differs between the state in which a magnetic field is applied to the object of measurement and the state in which a magnetic field is not applied. That is, in the case that a magnetic field is applied to the object of measurement, optical rotation occurs for various components in the object of measurement due to the Faraday effect, and hence the light transmitted through the object of measurement is subjected to optical rotation.

In the present embodiment, the constitution is such that light having a preset angle of optical rotation is selectively transmitted by the analyzer 13A, and this is received by the photoreceiver 13B. Light of what angle of optical rotation is received is determined, for example, in accordance with the type of the target component in the object of measurement and the magnitude of the magnetic field applied to the object of measurement; and further, an optical rotation angle may be experimentally selected by trial and error, by which angle the characteristic of the optical rotation by the target component can be most properly extracted.

In the case of measuring the concentration of glucose as the target component, the analyzer 13A is, for example, disposed in a state with the polarization axis thereof shifted by 1.0 to 10.0° in terms of the absolute value from the position of the polarization axis of the analyzer 13A at which the amount of light transmitted through the analyzer 13A is lowest (the extinction point), when linearly polarized light is irradiated onto the object of measurement in a state in which a magnetic field is not applied to the object of measurement.

The reception of the transmitted light by the photoreceiver 13B may be carried out with light of a single wavelength irradiated onto the fingertip 2, or maybe carried out separately for each wavelength with light of a plurality of wavelengths being separately irradiated.

As described above, in the calculation section 14B, the concentration of the target component in the object of measurement is calculated based on the amount of light received when the object of measurement is in the first magnetic field state and the amount of light received when the object of measurement is in the second magnetic field state. Here, an example of the procedure for calculating the concentration in the calculation section 14B will be described taking as an example the case of calculating the concentration of glucose.

Figure 3:
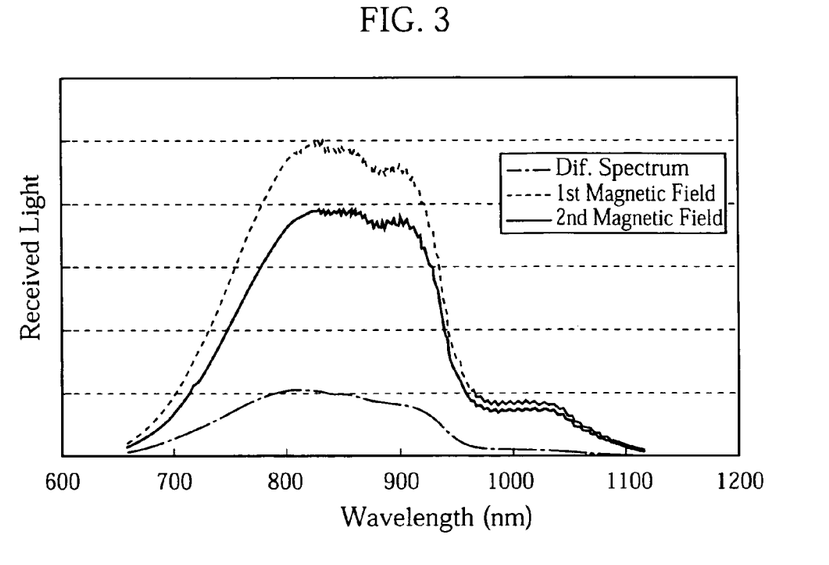
FIG. 3 is a graph showing, for a glucose solution, the absorption spectrum of rotated light having a specific oscillation plane in the case of applying a magnetic field to an object of measurement, the absorption spectrum in the case of not applying a magnetic field, and an absorption spectrum showing the difference between these absorption spectra.

With the concentration measuring device 1 shown in FIGS. 1 and 2, in the case that light of a specific angle of optical rotation is received for a plurality of wavelengths by the photoreceiver 13B, taking the amount of light received as a basis, spectra as shown by the full line and the dashed line in FIG. 3 are obtained. In FIG. 3, the full line is the spectrum in a state in which a magnetic field is not applied to the object of measurement (the second magnetic field state), and the dashed line is the spectrum in a state in which a magnetic field is applied to the object of measurement (the first magnetic field state). In FIG. 3, the differential spectrum between the spectrum in the first magnetic field state and the spectrum in the second magnetic field state is further shown as an alternate long and short dashed line.

Here, the differential spectrum is the sum of the amount of rotated light at a specific angle for the various components contained in the object of measurement, and hence the differential spectrum can be expressed by equation (1) below.

$$\text{Differential spectrum } (\lambda) = \Delta I_{glucose}(\lambda) + \Delta I_{water}(\lambda) + \Delta I_{noise}(\lambda) \quad (1)$$

$\Delta I_{glucose}(\lambda)$: Amount of rotated light for glucose
$\Delta I_{water}(\lambda)$: Amount of rotated light for water
$\Delta I_{noise}(\lambda)$: Amount of rotated light for noise components (light-diffusing components other than glucose and water)

From equation (1), it can be seen that the amount of rotated light for glucose $\Delta I_{glucose}(\lambda)$ can be determined by subtracting the amount of rotated light for water $\Delta I_{water}(\lambda)$ and the amount of rotated light for the noise components $\Delta I_{noise}(\lambda)$ from the differential spectrum $(\lambda)$. The amount of rotated light for glucose $\Delta I_{glucose}(\lambda)$ depends on the glucose concentration, and hence the glucose concentration can be calculated by determining the amount of rotated light for glucose $\Delta I_{glucose}(\lambda)$ In an abridged procedure, the effects of the noise components may be ignored, and in this case the amount of rotated light for glucose $\Delta I_{glucose}(\lambda)$ can be determined by subtracting the amount of rotated light for water $\Delta I_{water}(\lambda)$ from the differential spectrum$(\lambda)$.

In the abridged procedure, water fulfills the role of a reference, but something other than water may be used as a reference. For example, in the case of taking the effects of the noise components into consideration, the reference can be constructed so as to reflect the effects of the noise components. That is, a reference enabling the sum of the amount of rotated light for water $\Delta I_{water}(\lambda)$ and the amount of rotated light for the noise components $\Delta I_{noise}(\lambda)$ to be determined can be used. Moreover, two references corresponding respectively to the $\Delta I_{water}(\lambda)$ term and the $\Delta I_{noise}(\lambda)$ term in equation (1) may be used.

Taking the absorbance as a basis, equation (1) is equivalent to equation (2) below.

$$\text{Differential absorption spectrum}(\lambda) = \alpha \times Abs_{glucose}(\lambda) + \beta \times Abs_{water}(\lambda) + Noise(\lambda) \quad (2)$$

$\alpha$: Glucose spectrum coefficient
$\beta$: Water spectrum coefficient
$Abs_{glucose}(\lambda)$: Absorption spectrum due to optical rotation for glucose
$Abs_{water}(\lambda)$: Spectrum due to optical rotation for water
$Noise(\lambda)$: Remainder The absorbance at a targeted angle of optical rotation is related to the concentration of the target component, and hence by determining the coefficient $\alpha$ and the coefficient $\beta$ in equation (2), the proportions of glucose and water in the object of measurement can be determined. As a result, the ratio of glucose to water, and hence the glucose concentration, can be determined from the coefficient $\alpha$ and the coefficient $\beta$.

The coefficient $\alpha$ and the coefficient $\beta$ in equation (2) can be determined, for example, using a Singular Value Decomposition (SVD) procedure.

In an abridged calculation method, the Noise $(\lambda)$ term is ignored, and hence the coefficient $\alpha$ and the coefficient $\beta$ may be determined using the singular value decomposition procedure based on the $Abs_{glucose}(\lambda)$ term and the $Abs_{water}(\lambda)$ term. For example, if the absorption spectrum for the object of measurement and the absorption spectrum for water (the reference) are studied, then the absorption spectrum for glucose can be determined in pseudo fashion from the difference between these absorption spectra. The absorption spectrum for glucose can be determined for both when a magnetic field is applied to the object of measurement and when a magnetic field is not applied, and hence the absorption spectrum for glucose due to optical rotation $Abs_{glucose}$ (λ) can be determined. As a result, the coefficient α a and the coefficient β in equation (2) can be determined.

In the case of carrying out a more precise calculation, the coefficient α and the coefficient β may be determined by carrying out singular value decomposition with consideration given to the Noise(λ) term in equation (2). Here, the Noise(λ) term is the sum of the absorption spectra for components other than glucose and water, and precisely, can be expressed as in equation (3) below.

$$\text{Noise}(\lambda) = a \times \text{Abs}_{X1}(\lambda) + b \times \text{Abs}_{X2}(\lambda) + c \times \text{Abs}_{X3}(\lambda) + \ldots + n \times \text{Abs}_{Xn}(\lambda) \quad (3)$$

a, b, c, . . . , n: Coefficients $\text{Abs}_{Xn}(\lambda)$: Absorption spectrum for each individual component other than glucose and water Consequently, if the coefficient α and the coefficient β are determined by the singular value decomposition while optimizing a, b, c, . . . , n for the components other than glucose and water contained in the object of measurement, then a concentration calculation can be carried out in which consideration is also given to the effects of light-diffusing components that affect the glucose concentration measurement.

Moreover, in the case of calculating the glucose concentration based on equation (2), as in the case of calculating the glucose concentration based on equation (1) other references may be used instead of, or in addition to, water. Examples of references in this case are ones that reflect the effects of noise components.

Equation (2) can be used in the case that the object of measurement is a glucose solution held in a vessel, or in the case that the object of measurement is a body fluid (e.g. blood) contained in biological tissue such as a fingertip or an earlobe.

Here, in blood, as light-diffusing components other than glucose and water, typically there are components contained in the plasma, and oxyhemoglobin and reduced hemoglobin. Various components are contained in the plasma, but the present inventor has found that similar results are obtained in the case of determining the absorption spectrum for the plasma as a whole as in the case of determining the absorption spectrum due to optical rotation considering each component in the plasma separately and then summing these absorption spectra. Consequently, when calculating the glucose concentration, the differential absorption spectrum can be simply expressed as equation (4) below.

$$\text{Differential absorption spectrum}(\lambda) = \quad (4)$$
$$\alpha \times \text{Abs}_{glucose}(\lambda) + \beta \times \text{Abs}_{plasma}(\lambda) + $$
$$\gamma \times \text{Abs}_{oxyhemoglobin}(\lambda) + \delta \times \text{Abs}_{reduced\ hemoglobin}(\lambda)$$

α: Glucose spectrum coefficient
β: Plasma spectrum coefficient
γ: Oxyhemoglobin spectrum coefficient
δ: Reduced hemoglobin spectrum coefficient
$\text{Abs}_{glucose}(\lambda)$: Absorption spectrum due to optical rotation for glucose
$\text{Abs}_{plasma}(\lambda)$: Spectrum due to optical rotation for plasma
$\text{Abs}_{oxyhemoglobin}(\lambda)$: Spectrum due to optical rotation for oxyhemoglobin
$\text{Abs}_{reduced\ hemoglobin}(\lambda)$: Spectrum due to optical rotation for reduced hemoglobin In equation (4), plasma, oxyhemoglobin and reduced hemoglobin may be used together as three references, or one reference corresponding to plasma, oxyhemoglobin and reduced hemoglobin may be used. In the latter case, a lipid emulsion (fat emulsion for intravenous use) of concentration 0.5 to 2.0% for example may be used as the reference.

Next, second to fifth embodiments of the present invention will be described with reference to FIGS. 4 to 7. In FIGS. 4 to 7, elements the same as ones in the concentration measuring device according to the first embodiment of the present invention described earlier are designated by the same reference numerals, and in the following description, redundant description will be omitted.

Figure 4:
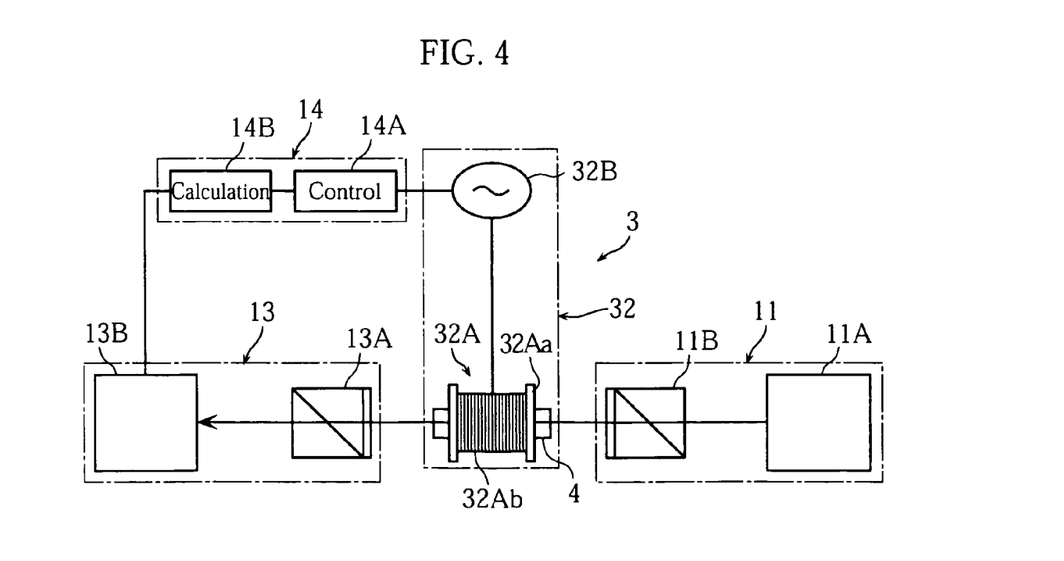
FIG. 4 is a conceptual view of a concentration measuring device according to a second embodiment of the present invention.

FIG. 4 shows a concentration measuring device according to a second embodiment of the present invention. Unlike the concentration measuring device 1 of the first embodiment, this concentration measuring device 3 is constituted such that a magnetic field applying section 32 comprises an electromagnet 32A and an alternating current generator 32B. The electromagnet 32A has a constitution in which a coil 32Ab is wound around a cylindrical magnetic core 32Aa.

With this constitution, an object of measurement 4 is disposed inside the magnetic core 32Aa, and a magnetic field applied to the object of measurement 4 is modulated through the control section 14A of the regulating circuitry 14, which controls the alternating current generator 32B so as to adjust the electrical power supplied to the electromagnet 32A.

With the concentration measuring device 3, the object of measurement 4 is disposed inside the magnetic core 32Aa, whereby the magnetic field is efficiently applied to the object of measurement 4.

Figure 5:
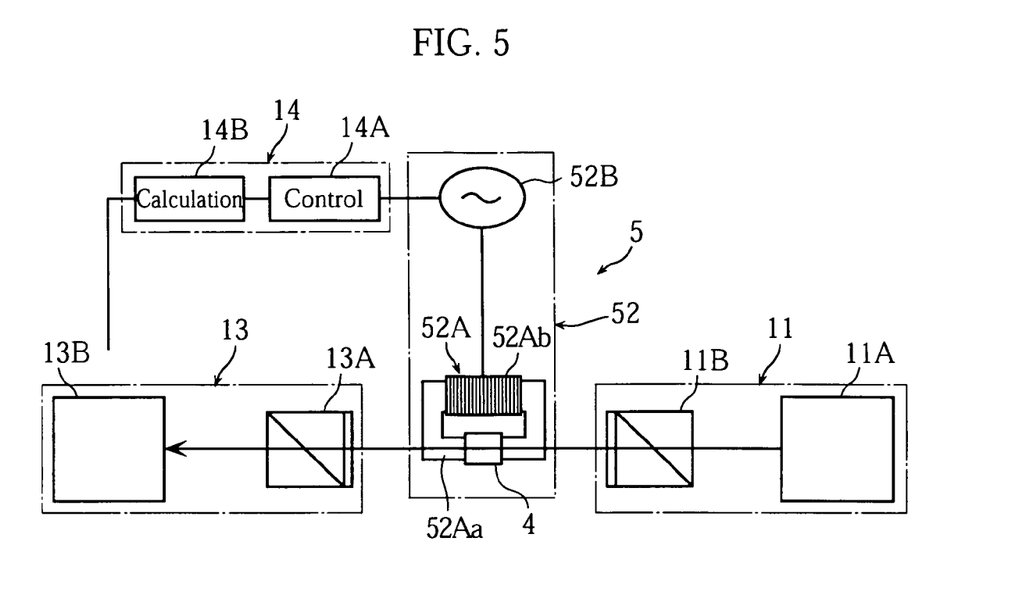
FIG. 5 is a conceptual view of a concentration measuring device according to a third embodiment of the present invention.

FIG. 5 shows a concentration measuring device according to a third embodiment of the present invention. This concentration measuring device 5 is like the concentration measuring device 3 according to the second embodiment of the present invention (see FIG. 4), except that the constitution of a magnetic field applying section 52 is different. The magnetic field applying section 52 is constituted such as to comprise an electromagnet 52A and an alternating current generator 52B. The electro magnet 52A has a constitution in which a coil 52Ab is wound around a magnetic core 52Aa. The magnetic core 52Aa is constituted such that two end portions thereof face one another, and the object of measurement 4 is disposed between these end portions.

With this constitution, the object of measurement 4 is disposed between the end portions of the magnetic core 52Aa, whereby a magnetic field is efficiently applied to the object of measurement 4. Moreover, not only an object of measurement in a state housed in a cell, but also a fingertip, an earlobe or the like can be disposed between the end portions of the magnetic core 52Aa, and hence this constitution is suitable for measuring the blood sugar value in a living body.

Figure 6:
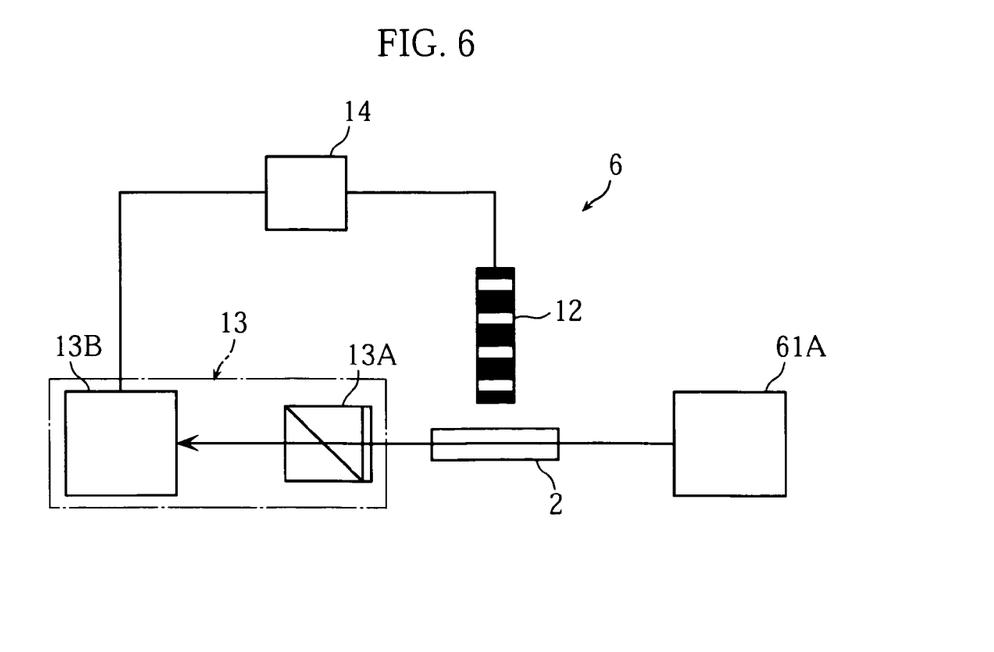
FIG. 6 is a conceptual view of a concentration measuring device according to a fourth embodiment of the present invention.

FIG. 6 shows a concentration measuring device according to a fourth embodiment of the present invention. This concentration measuring device 6 is like the concentration measuring device 1 according to the first embodiment of the present invention (see FIGS. 1 and 2), except that a laser light source 61A that emits linearly polarized light is used as the light irradiating section.

With this concentration measuring device 6, linearly polarized light is emitted from the laser light source 61A, whereby a polarizer 11B (see FIGS. 1 and 2) becomes unnecessary. Hence the constitution of the device can be simplified, and the light emitted from the light source can be utilized effectively.

Figure 7:
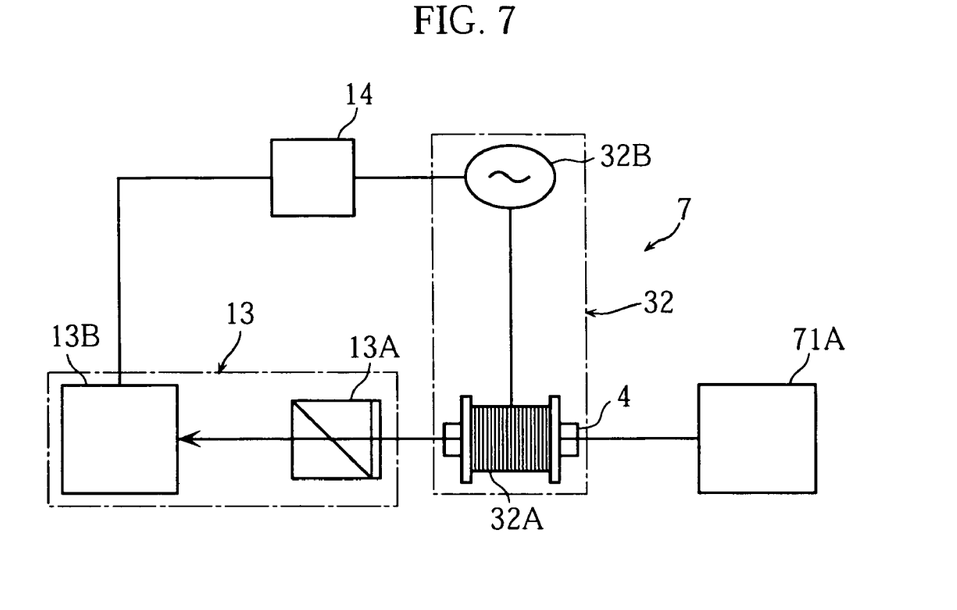
FIG. 7 is a conceptual view of a concentration measuring device according to a fifth embodiment of the present invention.

FIG. 7 shows a concentration measuring device according to a fifth embodiment of the present invention. This concentration measuring device 7 is like the concentration measuring device 3 according to the second embodiment of the present invention (see FIG. 4), except that a laser light source 71A that emits linearly polarized light is used as the light irradiating section.

With this concentration measuring device 7, as with the concentration measuring device 5 according to the third embodiment (see FIG. 5), a polarizer 11B (see FIGS. 1 and 2) becomes unnecessary, and hence the constitution of the device can be simplified, and the light emitted from the light source can be utilized effectively.

With the concentration measuring device 7, a magnetic field applying section 52 like that of the concentration measuring device 5 according to the third embodiment of the present invention (see FIG. 5) can be used.

In the embodiments described above, description is given with the case of measuring glucose concentration taken as an example; however, the present invention is not limited to glucose, but can also be used in the case of measuring other component concentrations. Furthermore, when measuring the glucose concentration or the like in a human body, the measurement site is not limited to a fingertip, but rather the present invention can also be used with an earlobe, for example.

EXAMPLES

Example 1

Figure 8:
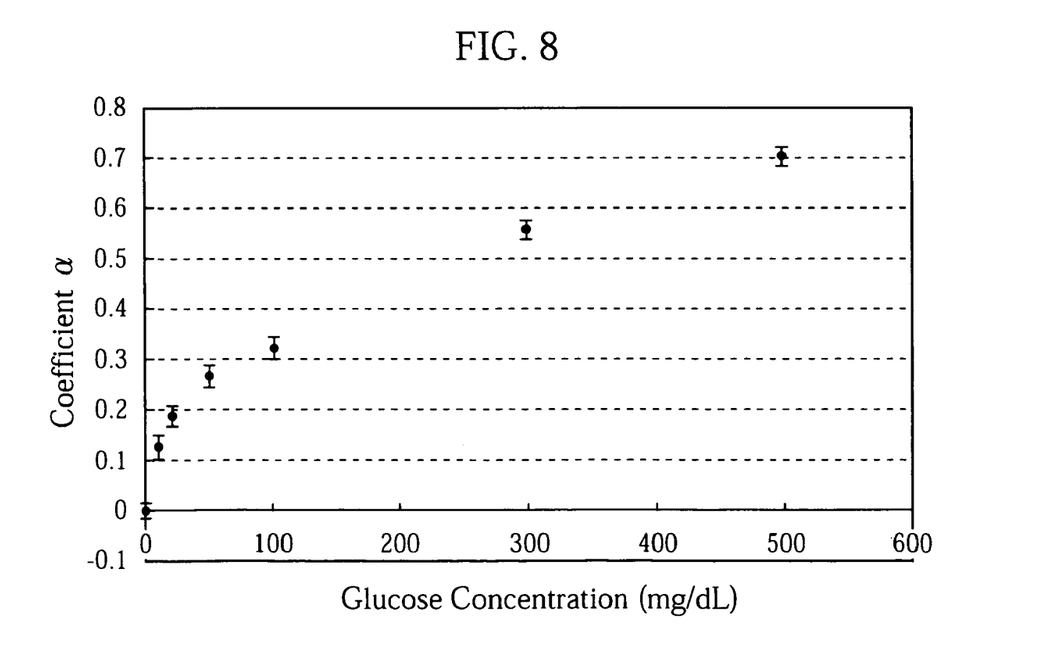
FIG. 8 is a graph showing calculation results for a coefficient α in Example 1.

In the present example, the coefficient α in equation (2) was determined through an abridged calculation method which ignores the noise(λ) term in equation (2). The results are shown in FIG. 8.

In the calculation of the coefficient α, the absorbance of objects of measurement and the absorbance of water (a reference) were measured.

In the absorbance measurements, each sample was put into a quartz cell having a cell length of 30 mm, and the amount of light transmitted upon irradiating light onto the quartz cell was measured.

As samples, seven glucose solutions of concentration 0 mg/dL (=pure water as the reference), 10 mg/dL, 20 mg/dL, 50 mg/dL, 100 mg/dL, 300 mg/dL and 500 mg/dL were used.

The irradiation of light onto the quartz cell was carried out after making light emitted from a halogen lamp close to parallel light using a lens, and then converting into linearly polarized light using a polarizer. The wavelength of the irradiated light was changed continuously in a range of 660 to 1110 nm.

The transmitted light was received continuously by a photodiode while changing the wavelength in both a state in which a magnetic field was applied onto the quartz cell and a state in which a magnetic field was not applied.

The application of the magnetic field onto the quartz cell was carried out using neodymium magnets (width 30 mm, height 50 mm, thickness 10 mm) such that the magnetic flux density at the center of the luminous flux of the light irradiated onto the quartz cell was 400 gauss, and the modulation frequency was 60 Hz.

At the photodiode, the light was received after filtering the transmitted light from the quartz cell into linearly polarized light having a targeted oscillation plane using an analyzer.

The analyzer was disposed with the polarization axis thereof shifted by 5° from a reference, the reference being taken as the orientation of the polarization axis at the extinction point (the point at which the intensity of the light transmitted by the analyzer is lowest when light transmitted through the quartz cell is made to be incident on the analyzer in the case that pure water has been put into the quartz cell and a magnetic field is not applied onto the quartz cell).

In FIG. 8, the horizontal axis shows the glucose concentration, and the vertical axis shows the coefficient α. As can be seen from FIG. 8, there is a fixed relationship between the glucose concentration and the coefficient α. Consequently, if the coefficient α is determined from the procedure described earlier, then the glucose concentration can be calculated.

Here, it should be noted that with the system on which the present experiments were carried out, the amount of water is approximately constant regardless of the sample concentration, and hence the coefficient β in equation (2) can be taken as a constant. The coefficient α should thus essentially be proportional to the glucose concentration. Regarding this point, there is room for improvement in future studies, but one reason for this is thought to be that a halogen lamp was used as the light source, and there was a problem with the optical system for making the light from the halogen lamp into parallel light. That is, it is thought that, due to the experiments being simple, the construction of the optical system was insufficient, and hence the light irradiated onto the quartz cell was not sufficiently parallel. It is thus thought that the measurement precision will be improved by increasing the degree of parallelity of the light irradiated onto the object of measurement.

Example 2

In the above, a description was given taking as an example the case of calculating the glucose concentration by irradiating light onto an object of measurement while continuously changing the wavelength; however, as can be amply anticipated from equation (2), the glucose concentration can be calculated based on equation (2) even in the case of irradiating light of a single wavelength. That is, equation (2) has been expressed as a relational expression for the differential absorption spectrum, but the relationship expressed in equation (2) also holds as a relational expression for the absorbance in the case of fixing at a single wavelength.

In the present example, a single wavelength was irradiated onto an object of measurement, and from the results of receiving the light at this time, the coefficient α and the coefficient β were determined through an abridged calculation ignoring the noise(λ) term in equation (2), and then the glucose concentration was measured from these coefficients α and β. The results are shown in FIG. 9.

Figure 9:
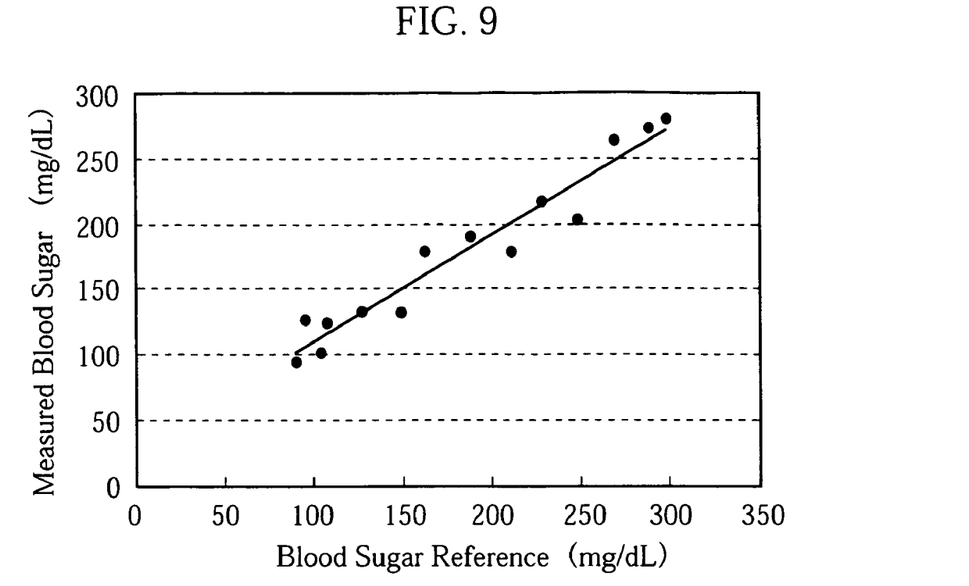
FIG. 9 is a graph of results of measuring glucose concentration in plasma in Example 2.

In FIG. 9, the results of measuring the blood sugar value of each sample using a blood sugar value measuring device (Glucocard GT-1160 made by Arkray) are shown as reference values on the horizontal axis.

In the absorbance measurements, each object of measurement was put into a quartz cell having a cell length of 30 mm, and the amount of light transmitted upon irradiating light onto the quartz cell was measured.

As the objects of measurement, samples of plasma having unknown glucose concentrations, and pure water as a reference were used.

The irradiation of light onto the quartz cell was carried out after making light emitted from a halogen lamp close to parallel light using a lens, and then converting into linearly polarized light using a polarizer. The wavelength of the irradiated light was fixed at 1064 nm.

The transmitted light was received by a photodiode in both a state in which a magnetic field was applied onto the quartz cell and a state in which a magnetic field was not applied.

The application of the magnetic field onto the quartz cell was carried out using neodymium magnets (width 30 mm, height 50 mm, thickness 10 mm) such that the magnetic flux density at the center of the luminous flux of the light irradiated onto the quartz cell was 400 gauss, and the modulation frequency was 60 Hz.

At the photodiode, targeted rotated light was received after filtering the transmitted light from the quartz cell into linearly polarized light having a targeted oscillation plane using an analyzer.

The analyzer was disposed with the polarization axis thereof shifted by 5° from a reference, the reference being taken as the orientation of the polarization axis at the extinction point.

As can be seen from FIG. 9, even in the case that the measurement wavelength was fixed, a good correlation was obtained with the case in which the blood sugar value measuring device was used. Moreover, in the present experiments, plasma containing noise components was used as the samples, and the glucose concentration was calculated through an abridged procedure ignoring the Noise($\lambda$) term in equation (2). It is thus thought that results correlating yet better with the measurement results from the blood sugar value measuring device would be obtained if calculations taking the Noise($\lambda$) term into consideration were carried out.

Example 3

In the present example, the coefficient $\alpha$ in equation (2) was determined essentially as in Example 1, except that a titanium sapphire laser oscillator (made by Spectra-Physics) was used as the light source. The results are shown in FIG. 10.

It should be noted, however, that six glucose solutions of concentration 0 mg/dL (=pure water as a reference), 10 mg/dL, 20 mg/dL, 50 mg/dL, 100 mg/dL and 300 mg/dL were used as samples. Moreover, the application of the magnetic field onto the quartz cell was carried out with a modulation frequency of 60 Hz such that the magnetic flux density at the center of the luminous flux of the light irradiated onto the quartz cell was 1000 gauss.

Figure 10:
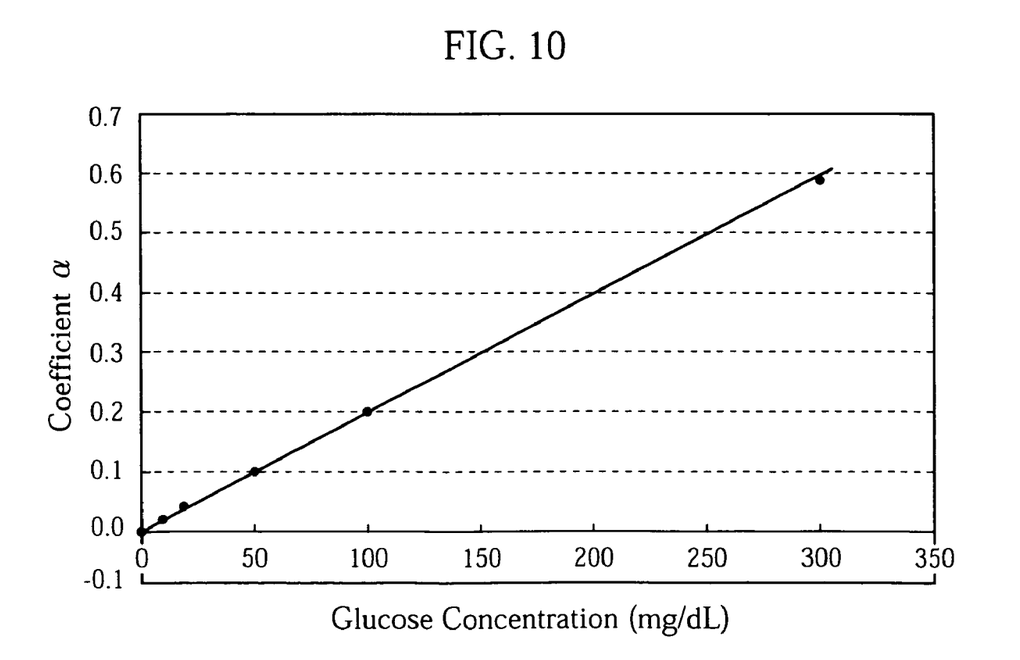
FIG. 10 is a graph showing calculation results for the coefficient α in Example 3.

In FIG. 10, the horizontal axis shows the glucose concentration, and the vertical axis shows the coefficient $\alpha$; a good correlation is seen between the glucose concentration and the coefficient $\alpha$. The constitution of the light irradiating section differs greatly between Example 1 and Example 3, and the result of this appears as a difference in the degree of linearity between Example 1 (FIG. 8) and Example 3 (FIG. 10). It is thus thought that by irradiating light having a high degree of parallelity onto the object of measurement as in the present example, the measurement precision can be improved.

Example 4

Figure 11:
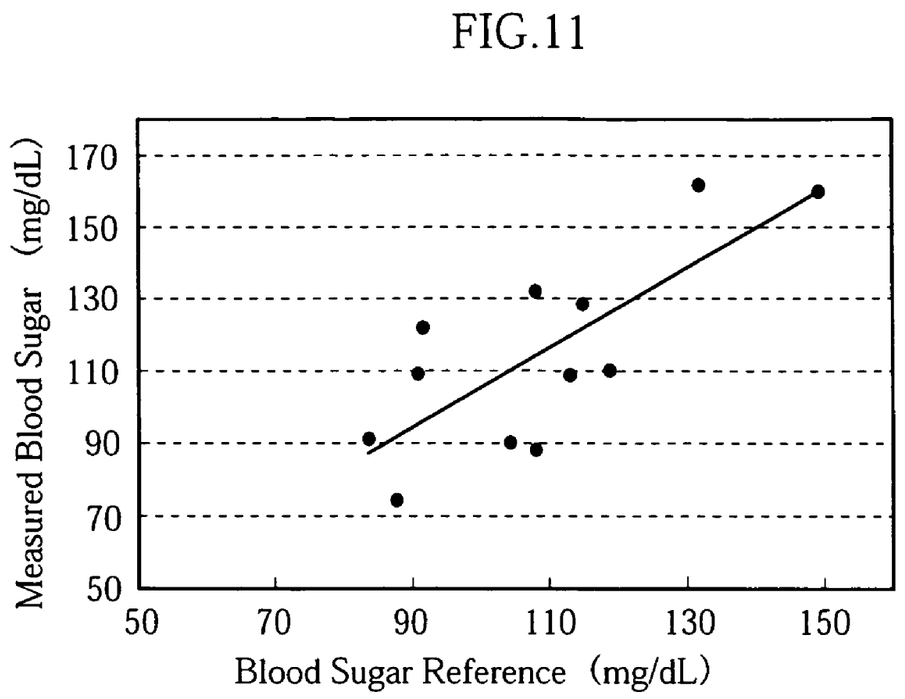
FIG. 11 is a graph of results of measuring glucose concentration in fingertips in Example 4.

In the present example, glucose concentration was measured using subjects' fingers as objects of measurement. The results are shown in FIG. 11. In FIG. 11, again glucose concentrations measured using a blood sugar value measuring device as in Example 2 are shown as reference values on the horizontal axis.

There were a total of four subjects, three men (one in his 30's, two in their 40's) and one woman (in her 30's), all of the subjects being healthy persons.

The glucose concentration measurement site was made to be the tip of the little finger, and the glucose concentration was measured before and after each subject had a meal.

Light of wavelength 1064 nm was made close to parallel light using a lens, and then converted into linearly polarized light using a polarizer, before being irradiated onto the fingertip.

The light transmitted through the fingertip was passed through an analyzer, and then received by a photodiode in both a state in which a magnetic field was not applied onto the fingertip and a state in which a magnetic field was applied onto the fingertip.

The analyzer was disposed with the polarization axis thereof shifted by 15° from a reference, the reference being taken as the orientation of the polarization axis at the extinction point.

Regarding the magnetic field applied to the fingertip, the magnetic flux density at the center of the luminous flux of the light irradiated onto the fingertip was made to be 400 gauss, and the modulation frequency was made to be 60 Hz.

As a reference, a 1% lipid emulsion (for intravenous use) was used.

As can be seen from FIG. 11, some correlation is seen between the reference values and the calculated values, although the errors are somewhat large. With the present measurement results, as in the case of Example 2, it is thought that there was a problem with the degree of parallelity of the light irradiated onto the fingertips, and moreover it is also thought that there was a problem with the way of setting the reference. That is, the reference in the present example was an emulsion rather than pure water, and hence the reference was made to be one that takes into consideration the effects of noise components, but it is thought that this was not sufficient in the case of measurements on fingertips. It is thought that if, in the future, the problem of the degree of parallelity of the irradiated light can be resolved, and a suitable reference can be selected, then it will be possible to measure the glucose concentration accurately.

The invention claimed is:

1. A component concentration measurement method, comprising:
    a first step of irradiating light onto an object of measurement with the object of measurement in a first magnetic field state, and detecting a state of light from the object of measurement at this time;
    a second step of irradiating light onto the object of measurement with the object of measurement in a second magnetic field state different from the first magnetic field state, and detecting a state of light from the object of measurement at this time; and
    a third step of calculating the concentration of a target component based on a detection result in the first step and a detection result in the second step;
    wherein in the first and second steps, the state of light from the object of measurement is detected as the absorbance or the amount of light; and
    wherein in the third step, the concentration of the target component is calculated based on the difference $\Delta$ between the absorbance or the amount of light measured in the first step and the absorbance or the amount of light measured in the second step.

2. The component concentration measurement method according to claim 1, wherein the first magnetic field state is a magnetic-field-modulated state obtained by applying a magnetic field to the object of measurement from outside, the second magnetic field state being a non-magnetic-field-modulated state.

3. The component concentration measurement method according to claim 2, wherein the first magnetic field state is attained by applying a magnetic field to the object of measurement such that the magnetic flux density at the center of the luminous flux of the light irradiated onto the object of measurement is 100 to 1000 gauss.

4. The component concentration measurement method according to claim 1, wherein the light irradiated onto the object of measurement is linearly polarized light.

5. The component concentration measurement method according to claim 4, wherein in the first and second steps, the state of light from the object of measurement is detected after making the light into linearly polarized light using an analyzer.

6. The component concentration measurement method according to claim 5, wherein the analyzer is disposed so as to selectively transmit light having a different oscillation plane to the oscillation plane of the light irradiated onto the object of measurement.

7. The component concentration measurement method according to claim 6, wherein the analyzer is disposed in a state with the polarization axis thereof shifted by 1.0 to 10.0° in terms of the absolute value from a position of the polarization axis of the analyzer at which the amount of light transmitted by the analyzer is lowest when light is irradiated onto the object of measurement in the second magnetic field state.

8. The component concentration measurement method according to claim 1, wherein the absorbance or the amount of light is measured based on light transmitted through the object of measurement.

9. The component concentration measurement method according to claim 1, wherein in the third step, the coefficient $\alpha_1$ and the coefficient $\beta_1$ in following equation (1) are determined, and the concentration of the target component is calculated based on the coefficients $\alpha_1$ and $\beta_1$, $$\text{Difference } \Delta = \alpha_1 \times X_1 + \beta_1 \Delta Y_1 \quad (1)$$

$X_1$: Change in absorbance due to change in state of optical rotation for target component between first and second magnetic field states, $Y_1$: Change in absorbance due to state of optical rotation for at least one component other than target component between first and second magnetic field states.

10. The component concentration measurement method according to claim 9, wherein $X_1$ is determined by subtracting the change in the absorbance for a reference between the first and second magnetic field states from the change in the absorbance for the object of measurement between the first and second magnetic field states, and wherein $Y_1$ is determined as the change in the absorbance for the reference between the first and second magnetic field states.

11. The component concentration measurement method according to claim 10, wherein the reference is pure water.

12. The component concentration measurement method according to claim 10, wherein the reference is one in which a state containing noise components is constructed in pseudo fashion.

13. The component concentration measurement method according to claim 9, wherein the target component is blood sugar and in measuring a blood sugar value, $X_1$ in equation (1) is determined as the change in the absorbance due to a change in the state of optical rotation for glucose between the first and second magnetic field states, wherein the calculation is carried out with the term $\beta_1 \times Y_1$ in equation (1) represented by following equation (2), $$\beta_1 \times Y_1 = \beta_{11} \times Y_{11} + \beta_{12} \times Y_{12} + \beta_{13} \times Y_{13} \quad (2),$$

wherein in equation (2), $\beta_{11}$, $\beta_{12}$ and $\beta_{13}$ are respectively a coefficient for plasma, a coefficient for oxyhemoglobin and a coefficient for reduced hemoglobin, wherein $Y_{11}$, $Y_{12}$ and $Y_{13}$ are respectively the change in the absorbance due to a change in the state of optical rotation for plasma, oxyhemoglobin and reduced hemoglobin between the first and second magnetic field states.

14. The component concentration measurement method according to claim 1, wherein in the first and second steps, a spectrum is obtained by measuring the absorbance or the amount of light at a plurality of wavelengths for the object of measurement and a reference, and in the third step, the difference $\Delta$ is obtained as a spectrum, and the coefficient $\alpha_2$ and the coefficient $\beta_2$ in following equation (3) are determined, and the concentration of the target component is calculated based on the coefficients $\alpha_2$ and $\beta_2$, $$\text{Difference } \Delta = \alpha_2 \times X_2 + \beta_2 \times Y_2 \quad (3)$$

$X_2$: Spectrum of change in absorbance due to change in state of optical rotation for target component between first and second magnetic field states, $Y_2$: Spectrum of change in absorbance due to state of optical rotation for at least one component other than target component between first and second magnetic field states.

15. The component concentration measurement method according to claim 14, wherein $X_2$ is determined by subtracting the spectrum of the change in the absorbance for the reference from the spectrum of the change in the absorbance for the object of measurement, and wherein $Y_2$ is determined as the spectrum of the change in the absorbance for the reference.

16. The component concentration measurement method according to claim 14, wherein the target component is blood sugar and in measuring a blood sugar value, $X_2$ in equation (3) is determined as the spectrum of the change in the absorbance due to a change in the state of optical rotation for glucose between the first and second magnetic field states, and the calculation is carried out with the term $\beta_2 \times Y_2$ in equation (3) represented by following equation (4), $$\beta_2 \times Y_2 = \beta_{21} \times Y_{21} + \beta_{22} \times Y_{22} + \beta_{23} \times Y_{23} \quad (4),$$

wherein in equation (4), $\beta_{21}$, $\beta_{22}$ and $\beta_{23}$ are respectively a coefficient for plasma, a coefficient for oxyhemoglobin and a coefficient for reduced hemoglobin, and wherein $Y_{21}$, $Y_{22}$ and $Y_{23}$ are respectively the spectrum of the change in the absorbance due to a change in the state of optical rotation for plasma, oxyhemoglobin and reduced hemoglobin between the first and second magnetic field states.

17. The component concentration measurement method according to claim 14, wherein the reference is pure water.

18. The component concentration measurement method according to claim 14, wherein the reference is one in which a state containing noise components is constructed in pseudo fashion.

19. The component concentration measurement method according to claim 14, wherein the coefficients $\alpha_2$ and $\beta_2$ are determined based on a singular value decomposition procedure.

20. The component concentration measurement method according to claim 1, wherein the target component of which the concentration is measured is glucose.

21. The component concentration measurement method according to claim 20, wherein the wavelength of the light irradiated onto the object of measurement is selected from a range of 780 to 1320 nm.

22. The component concentration measurement method according to claim 1, wherein the first and second steps are carried out by irradiating light directly onto a target component in a human body.

23. A component concentration measurement device, comprising:
   a magnetic field applier for applying a magnetic field to an object of measurement from outside;
   a controller for controlling the magnetic field applier to produce a first state in which the magnetic field applier does not apply a magnetic field to the object of measurement and a second state in which the magnetic field applier applies a magnetic field to the object of measurement;
   a light irradiator for irradiating light onto the object of measurement in the first and second states, respectively;
   a light receiver for receiving light from the object of measurement in the first and second states, respectively; and
   a calculator for calculating concentration of a target component contained in the object of measurement based on results of light reception by the light receiver in the first and second states.

24. The component concentration measurement device according to claim 23, wherein the light irradiator emits linearly polarized light.

25. The component concentration measurement device according to claim 24, wherein the light irradiator comprises a laser light source.

26. The component concentration measurement device according to claim 24, further comprising an analyzer for making light to be received by the light receiver into linearly polarized light.

27. The component concentration measurement device according to claim 26, wherein the analyzer has a polarization axis thereof disposed so as to selectively transmit linearly polarized light having a different oscillation plane from an oscillation plane of the linearly polarized light emitted from the light irradiator.

28. The component concentration measurement device according to claim 23, wherein the light irradiator comprises a titanium sapphire laser.

29. The component concentration measurement device according to claim 23, wherein the magnetic field applier comprises a rotating magnetic plate or an electromagnet.

30. The component concentration measurement device according to claim 23, further comprising a fixer for fixing the light irradiator, the magnetic field applier and the light receiver with a desired positional relationship relative to a predetermined site on a human body.

31. The concentration measurement device according to claim 30, wherein the fixer is constituted such as to be suitable for fixing onto a fingertip or an earlobe.

* * * * *